United States Patent [19]

Augustine

[11] Patent Number: 5,697,963
[45] Date of Patent: Dec. 16, 1997

[54] THERMAL BLANKET FOR A PATIENT SITTING IN A CHAIR

[75] Inventor: Scott D. Augustine, Bloomington, Minn.

[73] Assignee: Augustine Medical, Inc., Eden Prairie, Minn.

[21] Appl. No.: 575,774

[22] Filed: Dec. 20, 1995

[51] Int. Cl.$^6$ ...................................................... A61F 7/00
[52] U.S. Cl. .......................... 607/108; 607/104; 607/109
[58] Field of Search ..................... 607/96, 104, 107–109, 607/114

[56] References Cited

U.S. PATENT DOCUMENTS

| | | |
|---|---|---|
| 750,179 | 1/1904 | Foglesong .................. 607/108 |
| 2,110,022 | 3/1938 | Kliestrath . |
| 2,512,559 | 6/1950 | Williams . |
| 2,601,189 | 6/1952 | Wales, Jr. . |
| 3,714,947 | 2/1973 | Hardy . |
| 4,572,188 | 2/1986 | Augustine et al. . |
| 4,576,169 | 3/1986 | Williams . |
| 5,125,238 | 6/1992 | Ragan et al. . |
| 5,184,612 | 2/1993 | Augustine .................. 607/104 |
| 5,300,101 | 4/1994 | Augustine et al. . |
| 5,300,102 | 4/1994 | Augustine et al. . |
| 5,324,320 | 6/1994 | Augustine et al. . |
| 5,336,250 | 8/1994 | Augustine . |
| 5,343,579 | 9/1994 | Dickerhoff et al. . |
| 5,350,417 | 9/1994 | Augustine . |
| 5,360,439 | 11/1994 | Dickerhoff et al. . |
| 5,405,370 | 4/1995 | Irani .......................... 607/104 |
| 5,405,371 | 4/1995 | Augustine et al. . |
| 5,443,488 | 8/1995 | Namenye et al. . |
| 5,514,169 | 5/1996 | Dickerhoff et al. . |

FOREIGN PATENT DOCUMENTS

| | | |
|---|---|---|
| 0 311 336 | 3/1988 | European Pat. Off. . |
| 3308553 A1 | 10/1983 | Germany . |
| WO 85/03216 | 1/1985 | WIPO . |

*Primary Examiner*—Jennifer Bahr
*Assistant Examiner*—Rosiland Kearney
*Attorney, Agent, or Firm*—Baker, Maxham, Jester & Meador

[57] ABSTRACT

A thermal blanket including an inflatable covering having a plurality of apertures for delivering a thermally-controlled medium to a patient sitting in a chair. The inflatable covering includes an upper sheet and a base sheet connected at a periphery. The periphery includes a shoulder-facing head section proximate to the head of the patient, a foot section opposite thereto, a first side section extending from the head section to the foot section, and a second side section opposite thereto. A non-inflatable shoulder drape is formed in the head section. The shoulder drape includes an aperture for accommodating the head of the sitting patient so that the thermal blanket is affixed to the sitting patient. An uninflatable first side drape is formed in the first side section and an uninflatable second side drape is formed in the second side section. An uninflatable foot drape may also be formed in the foot section of the inflatable covering.

22 Claims, 2 Drawing Sheets

THERMAL BLANKET FOR A PATIENT SITTING IN A CHAIR

BACKGROUND OF THE INVENTION

1. Field of the Invention

This invention relates generally to thermal blankets used in a medical setting to deliver a bath of thermally-controlled gaseous medium, such as warmed air, to a sitting patient.

2. Description of the Related Art

Thermal blanket prior art is disclosed in commonly-assigned U.S. Pat. No. 4,572,188 entitled "AIRFLOW COVER FOR CONTROLLING BODY TEMPERATURE" and U.S. Pat. No. 5,405,371 entitled "THERMAL BLANKET", both of which are expressly incorporated by reference herein. These two patents describe thermal blankets which include a plurality of communicating inflatable chambers. In these blankets, apertures are formed through lower blanket surfaces. These apertures open through the surfaces into the chambers. When inflated with warmed air, the pressure of the air in the chambers causes the air flow cover to inflate. The apertures formed on the bottoms of the thermal blankets provide air outlets for the warmed air. Therefore, these thermal blankets create an ambient environment about the patient, the thermal characteristics of which are determined by the temperature and pressure of the gaseous inflating medium. One use for an inflatable thermal blanket is treatment for hypothermia such as might occur post-operatively.

The prior art thermal blankets, such as those described in the above-cited patents, address the problem of warming a patient lying in a prone position. Therefore, while using these thermal blankets, an operating table, a hospital bed or a gurney is required to support the patient. In many instances, such as during and after major surgery, the patient is required to be on an operating table or in a hospital bed and in those instances, the prior art thermal blankets can be used to warm the patient.

However, there are circumstances under which a patient should be warmed while in a sitting position. An increasing number of minor surgeries are being performed on an "out-patient" basis rather than in extended hospital stays. Outpatients awaiting minor surgery can sometimes benefit from warming before and after surgery. Often, outpatients rest in lounge or office chairs before surgery, after surgery, and before discharge, rather than lying on a gurney or hospital bed. Therefore, there is a need for a thermal blanket that can accommodate a patient who is sitting in a chair.

SUMMARY OF THE INVENTION

In accordance with the objectives of this invention as described above and to overcome the limitations of the prior art, a thermal blanket is provided for convectively warming a patient sitting in a chair. The thermal blanket comprises an inflatable covering including an upper sheet and a base sheet that are attached at a plurality of locations to form an inflatable portion with a plurality of inflatable chambers. The base sheet includes a plurality of apertures that direct an inflating medium from the inflatable chambers toward the patient. The periphery of the inflatable covering includes a head section, a foot section opposite thereto, a first side section, and a second side section opposite thereto. A non-inflatable shoulder drape is formed in the head section. An aperture is formed in the non-inflatable shoulder drape for accommodating the head of a sitting patient and affixing the thermal blanket thereto. The covering may also include a non-inflatable first side drape formed in the first side section and a non-inflatable second side drape formed in the second side section. A non-inflatable foot drape may also be formed in the foot section. The shoulder drape, first side drape, second side drape, and foot drape all operate to entrap and retain warmed air proximate to the sitting patient.

In the operation of a preferred embodiment, a heater/blower that includes a compressor and a heater supplies heated air, under pressure, to an inlet opening in the inflatable covering. The heated, pressurized air is distributed throughout the inflatable chambers and flows to the patient through the apertures in the base sheet of the thermal blanket.

The foregoing, together with other objects, features and advantages of this invention, will become more apparent when referring to the following specification, claims and the accompanying drawings.

BRIEF DESCRIPTION OF THE PREFERRED EMBODIMENT

For a more complete understanding of this invention, reference is now made to the following detailed description of the embodiments as illustrated in the accompanying drawing, wherein.

DETAILED DESCRIPTION OF THE PREFERRED EMBODIMENT

This invention is described in a preferred embodiment in the following description with reference to the Figures, in which like numbers represent the same or similar elements. While this invention is described in terms of the best mode for achieving this invention's objectives, it will be appreciated by those skilled in the art that variations may be accomplished in view of these teachings without deviating from the spirit or scope of the invention.

Figure 1:
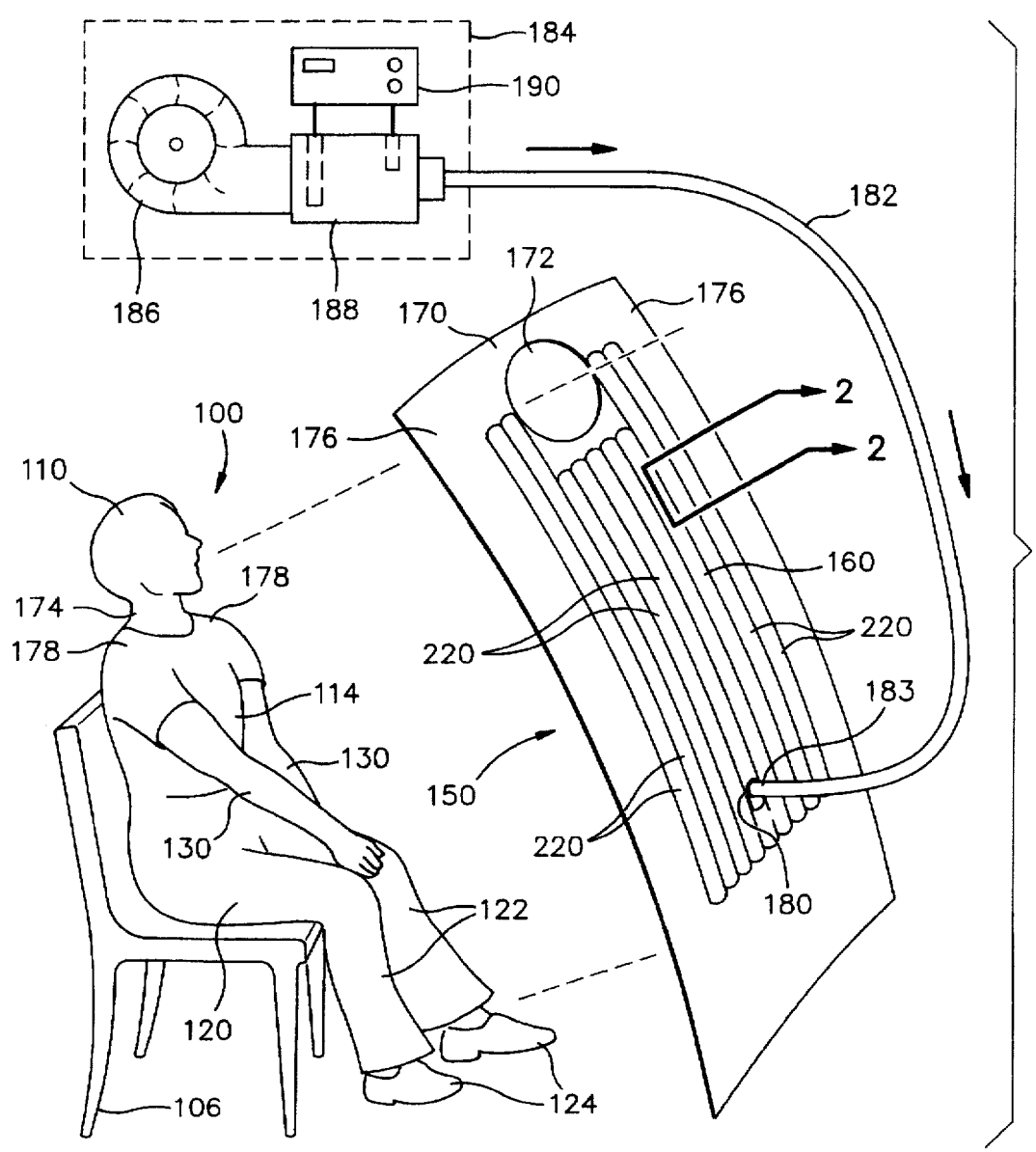
FIG. 1 is a perspective view of a sitting patient and a thermal blanket according to the invention with lead lines illustrating how the blanket would be received by the sitting patient, and also illustrating a forced-air heat pump for supplying heated air to the thermal blanket.

FIG. 1 illustrates a patient 100 in a sitting position on a chair 106. The chair 106 may be in doctor's office, in an out-patient facility associated with a hospital facility or any other suitable location. The patient 100 is illustrated with his head 110 positioned generally upright, his torso 114 positioned generally upright, his thighs 120 generally perpendicular to the floor, his lower legs 122 extending downwardly to the floor, and his feet 124 resting upon the floor. The patient's arms 130 are illustrated drawn in to his sides.

The patient sitting upright in a chair is illustrated to show the most extreme condition of use. It should be recognized that the patient could be partially reclining in a "recliner" chair with his legs and feet slightly elevated.

An inflatable thermal blanket indicated by reference numeral 150 is shown with connecting lines that illustrate how it would be attached to the patient 100. The thermal blanket 150 includes an inflatable section 160 surrounded by a non-inflatable section 176 that includes a shoulder drape 170 having a head opening 172 formed therein. The head opening 172 has a size to accommodate the head 110 and to rest around neck 174 of the patient.

The inflatable section 160 includes an inlet 180 that receives warmed air to pressurize and inflate it. The warmed air is provided by an airhose 182 from a forced-air heating unit 184 that includes a compressor 186 coupled to a heater 188. A control unit 190 controls the forced-air unit 184, and may include user-selectable fan speeds, controllable heat amounts, and temperature control. The inlet 180 in the inflatable section may be provided with a cuff or other conventional connector adapted to receive and retain the distal end 183 of the airhose 182. Using this configuration, pressurized and heated air can flow through the airhose 182 into the inflatable covering 160.

The inflatable thermal blanket of this invention may be constructed using methods and materials that are known for making similar products. A description of construction details suitable for making the thermal blanket of this invention is found in commonly-assigned U.S. Pat. No. 5,405,371, which has been incorporated by reference herein.

Figure 2:
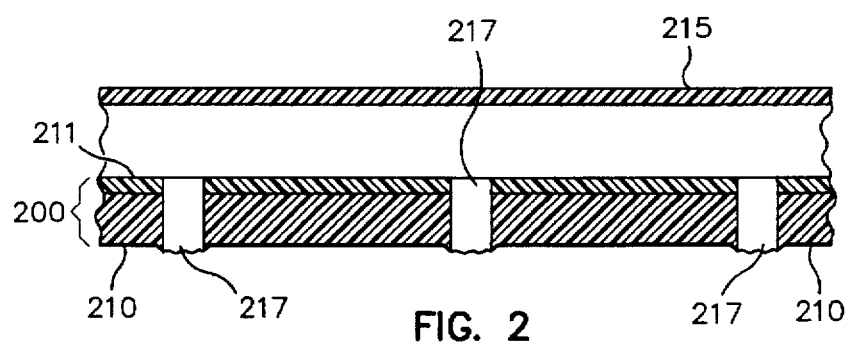
FIG. 2 is a perspective view along the cross-section shown in FIG. 1, illustrating an inflatable chamber and air outlet apertures on a bottom layer that allow airflow therethrough.
Figure 3:
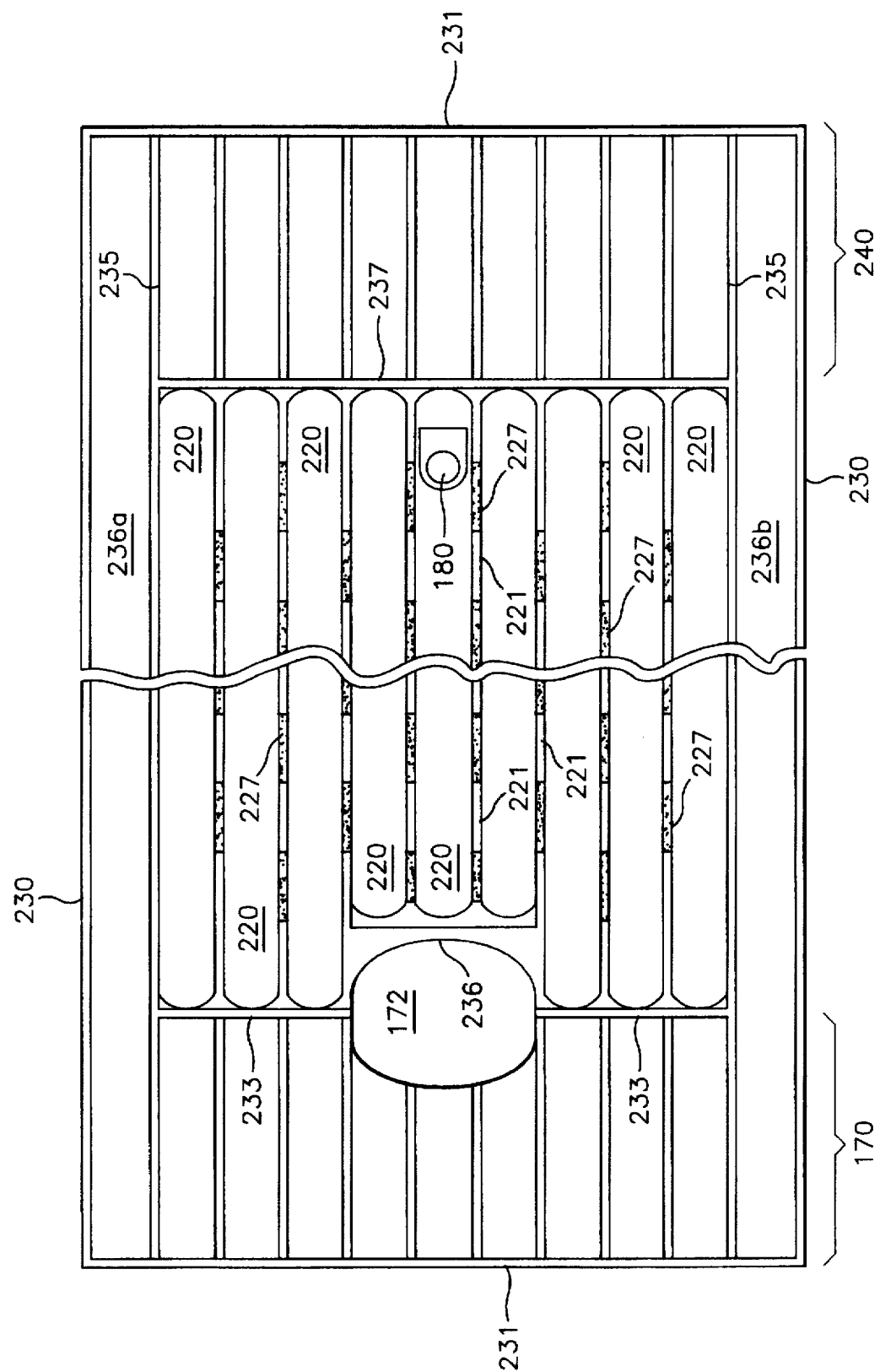
FIG. 3 is a top plan view of a thermal blanket for a sitting patient.

With reference now to the incorporated U.S. Pat. No. 5,405,371 blanket and to FIGS. 1–3, the thermal blanket 150 is assembled from a base sheet 200 having a laminated structure in which a bottom layer 210 comprises a fibrous, preferably non-woven structure composed of synthetic or natural materials. A top layer 211, comprising a sheet of synthetic material, is disposed on and laminated to a surface of the bottom layer 210. For example, the bottom layer 210 may be a non-woven, hydroentangled polyester material and the top layer may include a polypropylene film extrusion-coated on to the polyester layer. Alternatively, the bottom layer 210 may comprise a non-woven, paper-based material to which a top layer including either a polyethylene or a polypropylene film has been glue laminated. To form one or more inflatable chambers, an upper sheet 215 of material is attached at a plurality of locations to the top layer 211. Preferably, the upper sheet 215 comprises the same material as the top layer 211 of the base sheet 200. The upper sheet 215 is attached to the top layer 211 in the preferred embodiment in a continuously-running web process that includes stations at which the upper sheet 215 is heat-bonded to the top layer 211 to form the inflatable and non-inflatable sections of the thermal blanket 150. The inflatable chambers are shown in FIGS. 1 and 3 as having a generally elongate tubular shape. The inflatable chambers (which form the inflatable section 160) are indicated by reference numeral 220. The inflatable chambers 220 are preferably formed by discontinuous elongate heat seals. One example of an elongate discontinuous heat seal is shown having sealed portions 221 and unsealed portions 227. At the sealed portions 221 of the discontinuous elongate heat seal, the top layer 211 of the base sheet 200 is bonded to the upper sheet 215 in an elongate, air impermeable seam. Where the discontinuities 227 occur, air may circulate laterally between inflatable chambers. These discontinuities provide communication between the inflatable chambers, permitting pressurized, warmed air to circulate from the inlet 180 to, and through, the inflatable chambers 220. It should be understood that the inflatable chambers could be formed by a plurality of stake-point seals or by longer elongate seals. The plurality of apertures 217 that open through the base sheet 200 exhaust pressurized warmed air from the inflatable chambers 220 underneath the thermal blanket to bathe the patient 100 in a warmed ambient atmosphere.

Continuous, air impervious seals are shown in the top plan view of the thermal blanket of FIG. 3. These continuous air-impervious seals form one or more uninflatable sections of the thermal blanket 150, including the uninflatable shoulder drape 170. As FIG. 3 shows, there are two, parallel continuous, air-impervious edge seals 235 that are near the respective sides of the thermal blanket and two continuous, air-impervious end seals 231 at either end of the thermal blanket. The perimeter of the thermal blanket 150 is therefore sealed by a continuous, air-impervious seal comprising the seals 235 and the seals 231. Other air-impervious seals are used to selectively define non-inflatable sections of the blanket. In this regard, continuous, air-impervious seals 233 extending from respective edges of the head opening 172, toward respective sides of the thermal blanket define and close off the shoulder drape 170 to circulation of inflating air from the inflatable section 160. The seals 233, cooperating with an air-impervious sealed area 235 around the lower periphery 236 of the head opening 172, close off ends of the inflatable chambers 220 of the thermal blanket. These seals 235, together with the edges 230 form respective first and second uninflatable side sections 236a and 236b. Additionally, a continuous, air-impervious seal 237 extending between the seals 235 and offset inwardly from the bottom seal 231 toward the center of the thermal blanket forms an uninflatable foot drape section 240. The seal 237 also closes ends at the inflatable chambers 220.

Although four uninflatable sections, extending generally around the periphery of the thermal blanket, are shown, it is contemplated that a minimum of one uninflatable section, that being the shoulder drape 170, is required to practice the invention. This permits the head opening 172 to be formed effectively and efficiently in a web manufacturing process by simply stamping or curing in the uninflatable shoulder drape 170. This enables the thermal blanket to be placed over the head and about the neck of the patient and provides a short drape portion behind the neck, hanging down the patient's back. Draping the thermal blanket about the patient's neck ensures that the weight of the hose attached to the cuff at the inlet 180 will not drag the thermal blanket off of a sitting patient.

If desired, the uninflatable side sections (or, "drapes") 236a and 236b can be formed in the thermal blanket. The uninflatable side sections 236a and 236b, having more flexibility than the inflated section 160, permit the thermal blanket 150 to more adaptively fit to the contour of the sitting patient, and, in hanging down along the sides of the patient when the blanket is deployed for use, aid in trapping warm air under the thermal blanket.

Similarly, the foot drape 240 can be formed in the thermal blanket for the purpose of conforming the shape of the blanket, at least at its periphery, to the patient and entrapping heated air at the patient's feet.

The inflatable section of the blanket 160 has an approximately rectangular shape in the preferred embodiment which is dimensioned in width and length to approximately match the width of the shoulders 178 of the sitting patient and to approximately match a distance between the patient's shoulders and waist, or ankles (or any point there between). Of course, it will be recognized that because different patients have different shapes and sizes, different shapes and sizes of thermal blankets may be made available to accommodate most patients.

Other embodiments and modifications of this invention may occur to those of ordinary skill in the art in view of these teachings. Therefore, this invention is to be limited only by the following claims, which include all such embodiments and modifications when viewed in conjunction with the above specification and accompanying drawings.

What is claimed is:

1. An inflatable thermal blanket for convectively warming a patient comprising:
    an inflatable covering including an upper sheet and a base sheet connected together at a plurality of locations, said base sheet having a plurality of outlet apertures, said inflatable covering including an inflatable section, a head section, and a foot section opposite thereto; and
    a non-inflatable shoulder drape formed in said head section, said non-inflatable shoulder drape including an opening formed therein for accommodating the head of said patient.

2. The thermal blanket of claim 1, further including a non-inflatable first side drape at a first side of said inflatable section for extending along a first side of said patient; and
    a non-inflatable second side drape at a second side of said inflatable section for extending along side of said patient.

3. The thermal blanket of claim 1 wherein said inflatable section is adapted to extend substantially across the shoulders of said patient.

4. The thermal blanket of claim 3 wherein said inflatable section is adapted to extend substantially from the shoulders to the waist of said patient.

5. The thermal blanket of claim 3 wherein said inflatable section is adapted to extend substantially from the shoulders to the feet of said patient.

6. The thermal blanket of claim 1, further including a non inflatable foot drape formed in said foot section.

7. A thermal blanket system for warming a patient comprising:
    a source of heated air;
    an inflatable covering including an upper sheet and a base sheet connected together at a plurality of locations, said inflatable covering including an inlet opening coupled to said source for receiving heated air to inflate said inflatable covering, said base sheet having a plurality of outlet apertures for discharging the heated air toward the patient, said inflatable covering including a periphery with a head section, and a foot section opposite thereto; and
    a non-inflatable shoulder drape formed in said head section, said non-inflatable shoulder drape including an opening formed therein for accommodating the head of said patient.

8. The thermal blanket system of claim 7, the inflatable covering further including:
    an inflatable section;
    a non-inflatable first side drape at a first side of said inflatable section for extending along a first side of said patient; and
    a non-inflatable second side drape at a second side of said inflatable section for extending along a second side of said patient.

9. The thermal blanket system of claim 7, further including a non inflatable foot drape formed in said foot section.

10. The thermal blanket system of claim 7 wherein said inflatable covering is adapted to extend substantially across the shoulders of said patient.

11. The thermal blanket system of claim 7 wherein said inflatable covering is adapted to extend substantially from the shoulders to the waist of said patient.

12. The thermal blanket system of claim 7 wherein said inflatable covering is adapted to extend substantially across from the shoulders to the feet of said patient.

13. A flexible, inflatable thermal blanket comprising:
    an inflatable coveting including an upper sheet and a base sheet connected together at a plurality of locations that collectively define an inflatable section within a periphery including an uninflatable head section, a foot section opposite thereto, a first side section, and a second side section opposite thereto;
    an inlet opening into said inflatable section for inflating the inflatable covering; and,
    a hole in the uninflatable head section for receiving the neck of a patient.

14. The flexible, inflatable thermal blanket of claim 13 wherein said uninflatable head section includes an uninflatable shoulder drape formed in said inflatable covering, said uninflatable shoulder drape including said hole.

15. The flexible, inflatable thermal blanket of claim 13 further comprising a non-inflatable foot drape formed in the foot section.

16. The flexible, inflatable thermal blanket of claim 13 wherein said inflatable covering is adapted to extend substantially across the shoulders of said patient.

17. The flexible, inflatable thermal blanket of claim 13 wherein said inflatable covering is adapted to extend substantially from the shoulders to the waist of said patient.

18. The flexible, inflatable thermal blanket of claim 13 wherein said inflatable covering is adapted to extend substantially from the shoulders to the feet of said patient.

19. A patient warming system including the flexible, inflatable thermal blanket of claim 13, and further comprising:
    a source of pressurized, warmed air; and
    a hose connected to the source and to the inlet for conducting pressurized, warmed air to the inflatable covering.

20. The inflatable thermal blanket or claim 1, wherein the inflatable section comprises a plurality of communicating, inflatable chambers.

21. The thermal blanket system of claim 8, wherein the inflatable section includes a plurality of communicating, inflatable chambers.

22. The flexible, inflatable thermal blanket of claim 13, wherein the inflatable section comprises a plurality of communicating, inflatable chambers.

* * * * *

UNITED STATES PATENT AND TRADEMARK OFFICE
CERTIFICATE OF CORRECTION

PATENT NO. : 5,697,963
DATED : December 16, 1997
INVENTOR(S) : Augustine

It is certified that error appears in the above-indentified patent and that said Letters Patent is hereby corrected as shown below:

Column 5, line 17, insert --a second-- between "along" and "side".

Signed and Sealed this

Seventeenth Day of March, 1998

Attest:

BRUCE LEHMAN

Attesting Officer

Commissioner of Patents and Trademarks